United States Patent
Kotaka et al.

(12)

(10) Patent No.: US 6,461,159 B1
(45) Date of Patent: Oct. 8, 2002

(54) DENTAL MIXING PAD

(75) Inventors: Akiyoshi Kotaka, Tokyo (JP); Takeo Sasaki, Tokyo (JP); Makoto Michiaki, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/500,166

(22) Filed: Feb. 8, 2000

(30) Foreign Application Priority Data

Feb. 23, 1999 (JP) .......................................... 11-045203

(51) Int. Cl.[7] .............................................. A61C 19/00
(52) U.S. Cl. .......................... 433/49; 433/229; 433/226
(58) Field of Search ........................... 433/77, 49, 163, 433/229, 226; 206/369, 63.5

(56) References Cited

U.S. PATENT DOCUMENTS

| | | | | |
|---|---|---|---|---|
| 3,318,748 A | * | 5/1967 | Hurst | |
| 3,932,938 A | * | 1/1976 | Mackta | |
| 4,822,280 A | * | 4/1989 | Rider ........................ | 433/229 |
| 4,852,738 A | * | 8/1989 | Craig et al. ................. | 206/369 |
| 4,991,759 A | * | 2/1991 | Scharf ........................ | 224/217 |
| 5,106,297 A | * | 4/1992 | Discko, Jr. .................... | 433/77 |
| 5,139,188 A | * | 8/1992 | Scharf ........................ | 224/217 |
| 5,249,963 A | * | 10/1993 | McGarrigle ................. | 433/163 |
| 5,377,823 A | * | 1/1995 | Steen et al. ................. | 206/63.5 |
| 5,749,730 A | * | 5/1998 | Johnsen et al. ............. | 433/163 |
| 6,000,535 A | * | 12/1999 | Berk et al. ................. | 206/63.5 |

OTHER PUBLICATIONS

4yourparty.com—Item 43030/09 (7"Plastic Plates Yellow Sunshine) Item 43030/40 (Red/Apple Red).*

* cited by examiner

*Primary Examiner*—Ralph A. Lewis
(74) *Attorney, Agent, or Firm*—Oblon, Spivak, McClelland, Maier & Neustadt, P.C.

(57) ABSTRACT

A dental mixing pad whose mixing surface side is constituted by a color having a low reflectance of a light having a wavelength of 470 nm±80 nm, is disclosed. It is preferred that the color having a low reflectance of a light having a wavelength of 470 nm±80 nm, which constitutes the mixing surface side of the dental mixing pad, is satisfied with at least one of the following requirements: that is, in a standard illuminant $D_{65}$, $L^*$ is 80 or less, and $C^*$ is less than 20; $L^*$ is 80 or less, and h is 50°±80°; and $L^*$ is 30 or less, when expressed by an $L^*C^*h$ color space. The dental mixing pad of the present invention to be used as a substrate in mixing and kneading a dental material such as a dental cement or a resin-based material, using for dental adhesives or dental filling materials, on its mixing surface in the dental remedy, can readily suppress an unnecessary polymerization reaction with a illumination of circumferential lights without applying excessive operations or using a special device.

9 Claims, No Drawings

DENTAL MIXING PAD

BACKGROUND OF THE INVENTION

1. Field of the Invention

The present invention relates to a dental mixing pad that is used as a substrate in mixing and kneading a dental material such as a dental cement or a resin-based material, using for dental adhesives or dental filling-materials, on its mixing surface in the dental remedy. Particularly, the present invention relates to a dental mixing pad suitable for mixing and kneading a dental material such as the photopolymerization type dental cement.

2. Description of the Related Art

Hitherto, glass slab were employed as a mixing pad in mixing and kneading a dental material such as a dental cement or a resin-based material, using for dental adhesives or dental filling materials. However, they are liable to be broken, or are troublesome because they must be cleaned every time in use. Thus, in recent years, there have been used disposal mixing pads made of paper, synthetic paper, plastic film, plastic-coated paper, or the like.

For these disposable mixing pads, in order that a component to be mixed and kneaded (such as a cement powder or a cement liquid) does not penetrate or does not cause unnecessary chemical changes, or that a mixed material is easily taken out from its mixing surface, a paper having mixing surface coated with a plastic such as polypropylene or polyethylene, or a polypropylene film, a polyethylene film or the like, are used. In these mixing pads, the color to be used in the mixing surface side was generally white.

On the other hand, recently, photopolymerization type dental material such as a dental cement, a resin-based material, or the like and having a photopolymerization catalyst added thereto have become popularized. These dental materials are used for a desired purpose by filling in an oral cavity, etc. and then subjecting to polymerization and hardening through irradiation with a light. As described above, since the photopolymerization type dental material have such a characteristic that the reaction rapidly proceeds upon irradiation with a light, they involve a problem that the polymerization reaction proceeds even with a illumination of a circumferential light such as a shadowless lamp, a room lamp or sunlight in the circumference of remedy works, whereby the working time becomes short. Actually, there were problems that, in a case of a disease where it takes a time for filling operations, or in a case where after a dental hygienist has mixed a dental material on a mixing pad, for some reason, it takes a time for a dentist to use it, the photopolymerization reaction of the photopolymerization type dental material proceeds too much on the mixing surface, whereby the working time is lost, and that depending on circumstances, the photopolymerization type dental material is hardened before use, so that it is no longer useful, whereby the measuring and mixing and kneading operations of the dental material must be carried out again.

SUMMARY OF THE INVENTION

The present invention is aimed to provide a dental mixing pad which can decrease a polymerization reaction of a photopolymerization type dental materials which is caused by a illumination of circumferential lights to proceed too much, without using excessive operations or a special device, while overcoming the defects accompanied with the current dental mixing pad, for example, where the above-described current photopolymerization dental materials are used, decrease in working time, hardening of the material, due to the polymerization reaction with a illumination of circumferential lights.

In order to achieve the above-described aim, the present inventors made extensive and intensive investigations. As a result, they paid attention to that usually, in a photopolymerization type dental material, not only the polymerization from a surface of a mixed material occurs by direct lights, but also the polymerization is further accelerated by reflected lights on the surface of the dental mixing pad. Then, it has been found that when a mixing surface side of the dental mixing pad is constituted by a color having a low reflectance of a light having a wavelength of 470 nm±80 nm, at which a photopolymerization catalyst is excited, an excessive polymerization reaction of the photopolymerization type dental material by reflection from the surface of the dental mixing pad can be greatly suppressed and that the working time of the photopolymerization type dental material can be readily ensured, leading to the accomplishment of the present invention.

Further, it has been found that: it is preferred that the color having a low reflectance of a light having a wavelength of 470 nm±80 nm, which constitutes the mixing surface side of the dental mixing pad, is satisfied with at least one of the following requirements: that is, in a standard illuminant $D_{65}$, $L^*$ is 80 or less, and $C^*$ is less than 20; $L^*$ is 80 or less, and h is 50°±80° (i.e., from 0° to 130° and from 330° to 360°); and $L^*$ is 30 or less, when expressed by an $L^*C^*h$ color space.

DETAILED DESCRIPTION OF THE PREFERRED EMBODIMENTS

The dental mixing pad according to the present invention is described below in detail.

An excitation wavelength to be used for polymerization with visible lights in photopolymerization catalysts that are generally used as a photopolymerization type dental material is generally 470 nm±80 nm. For this reason, when the dental mixing pad is colored into a color where, among lights to be reflected from a mixing surface of the dental mixing pad, a light having a wavelength of 470 nm±80 nm has a light reflectance of 60% or less, and preferably 40% or less, a decrease in the working time can be remarkably suppressed.

The light having a wavelength of 470 nm±80 nm includes colors of a violet color (397 nm), an indigo color (431 nm), a deep blue color (486 nm), and a green color (527 nm) in terms of luminance spectrum. For this reason, when a mixing surface side of the mixing pad is constituted by a color having a low reflectance of a light having such a wavelength, the polymerization reaction caused by the reflection from the surface of the dental mixing pad of the photopolymerization type dental material can be readily suppressed, without applying excessive operations or using a special device. Specifically, suitable examples of the color that can lower the reflectance of a light having a wavelength of 470 nm±80 nm include a color having a low lightness and a low chroma (i.e. a low reflectance of the whole of visible lights) or a color having a low lightness and a long wavelength, inclusive of a yellow color (589nm), an orange color (636 nm), a crimson color (687 nm), and a deep red color (759 nm). When the mixing surface side of the dental mixing pad is constituted by such colors, the reflectance of a light having a wavelength of 470 nm±80 nm, at which the photopolymerization catalyst is excited, can be controlled to 60% or less.

The color having a low reflectance of a light having a wavelength of 470 nm±80 nm is a color that is satisfied with at least one of the following requirements: that is, in a standard illuminant $D_{65}$, L* is 80 or less, and C* is less than 20; L* is 80 or less, and h is 50°±80°; and L* is 30 or less, when expressed by an L*C*h color space. Incidentally, in the L*C*h color space, L* expresses a lightness of the color, C* expresses a chroma, and h is an index expressing a hue. When this color space is expressed in terms of an L*a*b* color specification as defined in JIS Z8729, "Specification of Colour of Materials according to the CIE1976 (L*a*b*) space and the CIE1976 (L*u*v*) Space", L*=L*, C*=$\{(a^*)^2+(b^*)^2\}^{1/2}$, and h=$\tan^{-1}$ (b*/a*).

In the L*C*h color space, the lightness is expressed by a numeral value L* of from 0 to 100, in which L*=0 means jet-black, and L*=100 means pure white. The higher or the lower the L* value, the less the influences of the hue or chroma are. In particular, in case where L* is higher than 80, the reflectance of all of the hues is high, and an effect for suppressing the polymerization reaction by a illumination of circumferential lights is low. Accordingly, it is preferred that L* is 80 or less.

In the L*C*h color space, C* represents a chroma and is expressed by numerical values of from 0 to 60. C* expresses a distance from the center point, crossing the a* and b* ordinates in the L*C*h color space. The smaller the C* value (the nearer to the center point), the lower the chroma is. In case where L* is 80 or less, and C* is less than 20, the reflectance of the light rays is low regardless of the h value as described below, thereby obtaining an effect for suppressing the polymerization reaction with a illumination of circumferential lights.

In the L*C*h color space, h represents a hue and is expressed by angles of from 0° to 360°. The h value represents an angle for the movement against a hue in the counterclockwise direction based on a coordinate in the red direction (+direction) of the a* coordinate in the L*C*h color space as defined to be 0. So far as the mixing surface of the dental mixing pad according to the present invention is constituted by a color having the L*=80 or less and a low reflectance of a light having a wavelength of 470 nm±80 nm inclusive of a yellow color (h=130°), an orange color (h=50°), and a deep red color (h=330°), i.e., within a range of 50°±80°, there gives rise to an effect for suppressing the polymerization reaction with a illumination of circumferential lights, regardless of the C* value.

Incidentally, in case where L* is 30 or less, the color becomes close to a black color, the reflectance of a light having a wavelength of 470nm±80nm can further be suppressed, regardless of the C*h values.

As for the photopolymerization catalyst to be used for the photopolymerization type dental material, a UV absorber may be applied simultaneously with the coloration, thereby improving an effect against the whole of a illumination of circumferential lights inclusive of a ultraviolet, etc. In this case, a degradation with a lapse of time of the dental mixing pad can also be prevented. Further, a coating having a matting effect may be used in combination.

As a raw material to be used for the dental mixing pad according to the present invention, those used for the current dental mixing pad and mixing substrates, such as plastic films, plastic-coated papers, and synthetic papers, can be used. For instance, the dental mixing pad according to the present invention is supplied in a filing state in which on a board composed of a square cardboard having a length of side of about 50 mm are stuck from about 20 to 100 sheets of a polypropylene-coated paper having the same size as in the board.

EXAMPLES (Colorimetry of Dental Mixing Pad)

Using a light source for colorimetry (a trade name: Sun Reamer, manufactured by Daiwa Lighting Co., Ltd.) as a light source, a light was irradiated from a position of 1 m away from a mixing surface side of a mixing pad. And, using a photodiode type spectrophotometer (a trade name: Spectrascan PR650, manufactured by Photo Research Co., Ltd.) as a calorimeter, a center portion having a diameter of 3 mm of the mixing pad surface on a light trap was measured at an angle of 45° against the mixing pad surface direction.

(Light Reflectance)

A reflectance of a light having a wavelength of 470 nm that is a main excitation wavelength of camphor quinone widely used as the photopolymerization initiator in a usual photopolymerization type dental material was measured by using the same apparatus as in the case of the colorimetry.

(Working Time)

On a mixing pad was weighed 1.0 g of a commercially available photopolymerization type composite resin (a trade name: Estio LC, A3 Color, manufactured by GC Corporation) as a photopolymerization type dental material, which was then irradiated with a light under the conditions of 1,000 lux by a fluorescent lamp (high-color rendering AAA natural white fluorescent lamp: 10 W×2) and 10,000 lux by a shadowless lamp, respectively. A time from the initiation of the light irradiation until the photopolymerization type dental material had been no longer shaped was defined as the working time.

Examples 1 to 4

A paper in which its mixing surface side had been colored into a desired color and then coated with a transparent polypropylene film was cut into a size of 50 mm in the longitudinal direction and 120 mm in the transverse direction. Thereafter, the color of the mixing surface side, the reflectance of a light having a wavelength of 470 nm, and the working time of the photopolymerization type dental material were measured. The results are shown in Table 1.

Examples 5 to 7

Using a Kent paper in which its mixing surface side had been colored into a desired color and then coated with a transparent polyvinyl chloride film, the color of the mixing surface side, the reflectance of a light having a wavelength of 470 nm, and the working time of the photopolymerization type of the dental material were measured. The results are also shown in Table 1.

Comparative Example 1

A color of a mixing surface side of a commercially available dental mixing pad (a trade name: Mixing Pad No. 22, manufactured by GC Corporation), its light reflectance, and a mixing pad of a photopolymerization type dental material were measured. The results are also shown in Table 1.

TABLE 1

| | Color | Results of colorimetry | | | Light reflectance (%) | Working time (min. & sec.) | |
|---|---|---|---|---|---|---|---|
| | | L* | C* | h | | 1,000 lux | 10,000 lux |
| Example 1 | Light red | 71 | 14 | 35 | 8 | 14' 08" | 1' 35" |
| Example 2 | Yellow | 52 | 52 | 93 | 35 | 12' 49" | 1' 27" |
| Example 3 | Black | 0 | 1 | 288 | 5 | 14' 10" | 1' 42" |
| Example 4 | Dark gray | 25 | 9 | 107 | 11 | 14' 02" | 1' 38" |
| Example 5 | Deep red | 60 | 24 | 357 | 17 | 13' 53" | 1' 32" |
| Example 6 | Light gray | 65 | 2 | 200 | 10 | 13' 59" | 1' 34" |
| Example 7 | Pink | 76 | 37 | 359 | 47 | 12' 35" | 1' 06" |
| Comparative Example 1 | White | 99 | 2 | 272 | 94 | 10' 20" | 0' 50" |

It can be understood from Table 1 that when the mixing surface side is constituted by a color having less than 60% reflectance of a light having a wavelength of 470 nm±80 nm, the polymerization reaction with a illumination of circumferential lights can be suppressed, whereby the working time of the photopolymerization type dental material can be ensured. In particular, it can be understood that, in Examples 1 to 6 in which the mixing surface side is constituted by a color having less than 40% reflectance of a light having a wavelength of 470 nm±80nm, a longer working time of the photopolymerization type dental material can be ensured.

In addition, it can also be understood that, in any of Examples 1, 3, 4 and 6 in which the color in the mixing surface side is satisfied with the requirements that, in a standard illuminant $D_{65}$, L* is 80 or less, and C* is less than 20, when expressed by an L*C*h color space; Examples 1, 2, 4, 5 and 7 in which the color in the mixing surface side is satisfied with the requirements that, in a standard illuminant $D_{65}$, L* is 80 or less, and h is 50°±80°, when expressed by an L*C*h color space; and Examples 3 and 4 in which the color in the mixing surface side is satisfied with the requirements that, in a standard illuminant $D_{65}$, L* is 30 or less, when expressed by an L*C*h color space, the working time of the photopolymerization type dental material can be ensured.

In the light of the above, as compared with the current mixing pad, the dental mixing pad according to the present invention has a low reflectance of a light having a wavelength at which the photopolymerization catalyst contained in the photopolymerization type dental material can be excited and can suppress the polymerization reaction with a illumination of circumferential lights, whereby the working time of the photopolymerization type dental material can be ensured. Further, the dental mixing pad according to the present invention can be used in mixing and kneading a dental material that is not of a photopolymerization type. Therefore, the present invention can greatly contributes to the dental field.

While the invention has been described in detail and with reference to specific embodiments thereof, it will be apparent to one skilled in the art that various changes and modifications can be made therein without departing from the spirit and scope thereof.

What is claimed is:

1. A method of reducing an amount of photopolymerization of a photopolymerizable dental material by light having a wavelength of 470 nm±80 nm reflecting from a surface of a dental mixing pad, comprising preparing said photopolymerizable dental material on said surface which has been colored with a color having a low reflectance of said light, and wherein the color is not black or gray.

2. The method of claim 1, wherein said mixing pad is made from a material comprising a plastic film, a plastic-coated paper, or a synthetic paper.

3. The method of claim 1, wherein the color satisfies the following requirements: in a standard illuminant $D_{65}$, L* is 80 or less, and C* is less than 20, when expressed by an L*C*h color space.

4. The method of claim 3, wherein the color satisfies the following requirements: in a standard illuminant $D_{65}$, L* is 80 or less, and h is 50°±80°, when expressed by an L*C*h color space.

5. The method of claim 4, wherein the color satisfies the following requirements: in a standard illuminant $D_{65}$, L* is 30 or less, when expressed by an L*C*h color space.

6. The method of claim 3, wherein the color satisfies the following requirements: in a standard illuminant $D_{65}$, L* is 30 or less, when expressed by an L*C*h color space.

7. The method of claim 1, wherein the color satisfies the following requirements: in a standard illuminant $D_{65}$, L* is 80 or less, and h is 50°±80°, when expressed by an L*C*h color space.

8. The method of claim 7, wherein the color satisfies the following requirements: in a standard illuminant $D_{65}$, L* is 30 or less, when expressed by an L*C*h color space.

9. The method of claim 1, wherein the color satisfies the following requirements: in a standard illuminant $D_{65}$, L* is 30 or less, when expressed by an L*C*h color space.

* * * * *